United States Patent
Fix et al.

(10) Patent No.: US 8,487,353 B2
(45) Date of Patent: Jul. 16, 2013

(54) ELECTRONIC COMPONENT

(75) Inventors: Richard Fix, Gerlingen (DE); Andreas Krauss, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 491 days.

(21) Appl. No.: 12/584,975

(22) Filed: Sep. 14, 2009

(65) Prior Publication Data
US 2010/0090255 A1  Apr. 15, 2010

(30) Foreign Application Priority Data

Oct. 15, 2008 (DE) .......................... 10 2008 042 859

(51) Int. Cl.
*H01L 49/00* (2006.01)

(52) U.S. Cl.
USPC ................ 257/253; 257/414; 257/E29.255; 438/49

(58) Field of Classification Search
USPC ................ 257/253, 414, E29.255; 438/49
See application file for complete search history.

(56) References Cited

U.S. PATENT DOCUMENTS

| | | | | |
|---|---|---|---|---|
| 4,650,561 A | * | 3/1987 | Robins et al. | 204/416 |
| 4,878,015 A | | 10/1989 | Schmidt et al. | |
| 4,913,792 A | * | 4/1990 | Nagata et al. | 204/412 |
| 5,457,333 A | * | 10/1995 | Fukui | 257/253 |
| 6,673,644 B2 | * | 1/2004 | Gole et al. | 438/49 |
| 8,001,828 B2 | * | 8/2011 | Hunter et al. | 73/31.06 |
| 8,072,008 B2 | * | 12/2011 | Mukasa et al. | 257/253 |
| 8,133,750 B2 | * | 3/2012 | Chou et al. | 438/49 |
| 2008/0012007 A1 | * | 1/2008 | Li et al. | 257/40 |
| 2008/0106276 A1 | * | 5/2008 | Penner et al. | 324/693 |
| 2008/0210987 A1 | * | 9/2008 | Bondavalli et al. | 257/253 |
| 2009/0084162 A1 | * | 4/2009 | Besnard et al. | 73/31.06 |
| 2010/0047948 A1 | * | 2/2010 | Ishida et al. | 438/49 |
| 2010/0109645 A1 | * | 5/2010 | Park et al. | 324/123 R |
| 2010/0155691 A1 | * | 6/2010 | Lee et al. | 257/9 |
| 2010/0327259 A1 | * | 12/2010 | Afzali-Ardakani et al. | 257/24 |

FOREIGN PATENT DOCUMENTS

| | | |
|---|---|---|
| DE | 3526348 | 2/1987 |
| DE | 101 61 213 | 7/2003 |
| DE | 101 61 214 | 7/2003 |
| DE | 10 2005 008 051 | 8/2006 |
| EP | 1 701 161 | 9/2006 |
| GB | 2 029 583 | 3/1980 |

* cited by examiner

*Primary Examiner* — Allan R Wilson
(74) *Attorney, Agent, or Firm* — Kenyon & Kenyon LLP

(57) ABSTRACT

An electronic component includes at least one electrode and at least one gas-sensitive region on a substrate. The gas-sensitive region is coated by at least one electrically conductive, gas-sensitive layer, and the electrode contacts the gas-sensitive layer. At least a part of the at least one electrode covers a part of the gas-sensitive region.

10 Claims, 4 Drawing Sheets

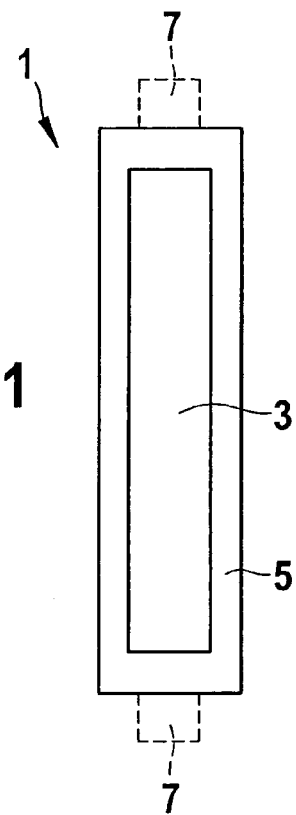
Fig. 3.1
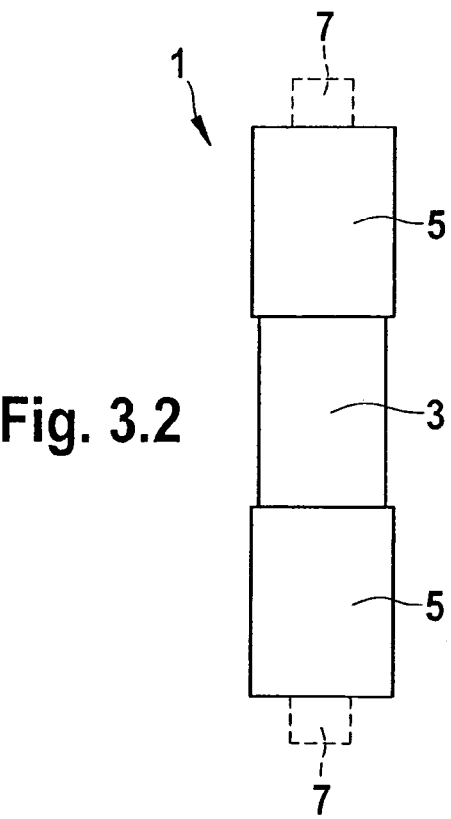
Fig. 3.2

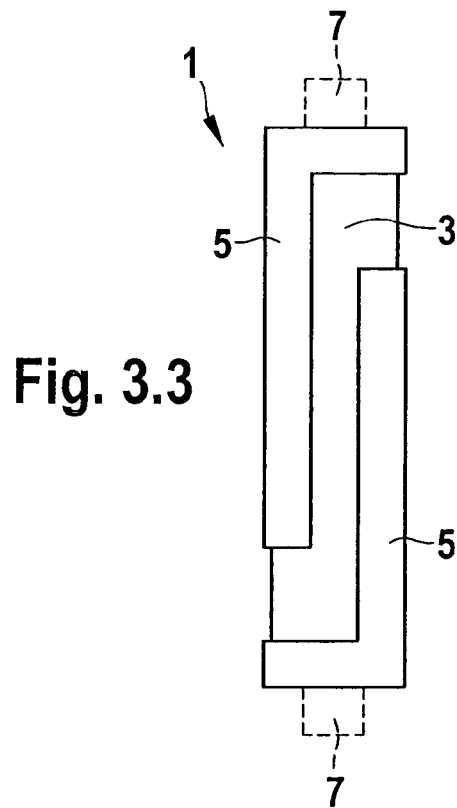
Fig. 3.3
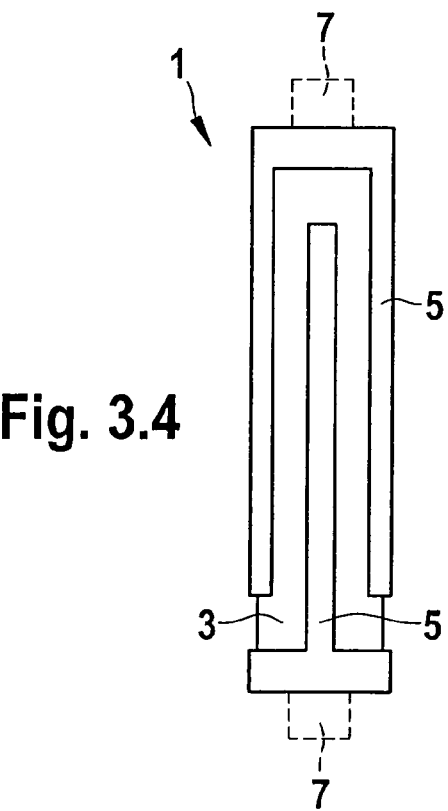
Fig. 3.4

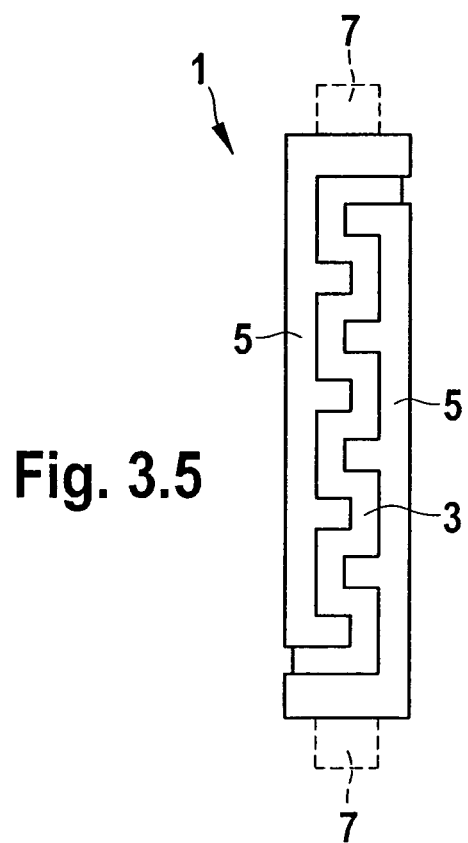
Fig. 3.5

ELECTRONIC COMPONENT

BACKGROUND OF THE INVENTION

1. Field of the Invention

The present invention relates to an electronic component, e.g., a gas-sensitive field effect transistor or a gas sensitive sensor.

2. Description of Related Art

Gas-sensitive field effect transistors are, for example, electronic components which have at least one electrode and at least one gas-sensitive region that is lined with at least one gas-sensitive layer. These are used to detect certain gas species in a gas stream. For this purpose, the at least one gas-sensitive layer is selected so that the most specifically possible gas reactions are achieved. The gas-sensitive layers for this generally contain metallic components, which are partially catalytically active and are partially present in nanocrystalline form. In order to make possible a rapid gas reaction, the gas-sensitive layers are generally very thin and at least partially porous. Because of the porosity, a large specific surface is achieved, through which the gas reaction is able to be speeded up.

In order to set a working point for the field effect transistor working as a signal transmitter, it is necessary to contact the at least one gas-sensitive layer electrically. Because of the gas reaction on the gas-sensitive layer, the resulting potential acting on the channel of the field effect transistor then changes, and with that, the current through the transistor. In order to achieve as great as possible a gas reaction, and with that, as great as possible a change in the resulting potential, in the field effect transistors known from the related art, if possible, the entire gas-sensitive region is lined with the gas-sensitive layer, and the electrodes are positioned outside the gas-sensitive region.

In the case of currently produced, gas-sensitive field effect transistors, the electrodes for the electrical connection of the gas-sensitive materials of the gas-sensitive layer are already applied during processing of the signal transmitter. In general, these have a different composition and a different construction from the gas-sensitive material. This may lead to problems, such as edge breaks at the contacting locations between the electrode and the gas-sensitive layer, in the case of components that are highly stressed thermally.

BRIEF SUMMARY OF THE INVENTION

An electronic component according to the present invention includes at least one electrode and at least one gas-sensitive region that is lined with at least one electrically conductive, gas-sensitive layer. The electrode contacts the gas-sensitive layer. At least one part of the at least one electrode covers a part of the gas-sensitive region.

Because of the covering of a part of the gas-sensitive region by the at least one electrode, a durable, reliable and validatable contacting of the gas-sensitive layer is achieved.

A further advantage of the electronic component developed according to the present invention is that a functioning test is able to be carried out during production, before the gas-sensitive layer is applied. This is possible because the at least one electrode covers a part of the gas-sensitive region, which acts as a gate region, and thus, differently from the field effect transistors known from the related art, directly contacts the gas-sensitive region that acts as a gate region.

The material, of which the at least one electrode is made, is preferably a noble metal, such as palladium, platinum, gold, rhenium, ruthenium and alloys of these, or an electrically conductive and chemically stable material such as titanium, titanium nitride or tantalum nitride. In order to improve the adherence to semiconductors of noble metals as material for the electrode, such as to gallium nitride or silicon carbide, titanium, zirconium, titanium nitride, tantalum silicide, nickel-chromium alloys and their corresponding oxides are frequently used.

As the material for the gas-sensitive region acting as the gate region, insulating materials are suitable, for instance, oxides such as silicon oxide ($SiO_2$), aluminum oxide ($Al_2O_3$), zirconium oxide ($ZrO_2$) or hafnium oxide ($HfO_2$), nitrides such as silicon nitride ($Si_3N_4$) or boron nitride (BN), carbides such as silicon carbide (SiC) as well as silicides such as tantalum silicide ($TaSi_2$) or tungsten silicide ($WSi_2$) or diamond.

The material of which at least one gas-sensitive layer is produced, is preferably selected from the group consisting of noble metals, such as palladium, platinum, gold, rhenium, rhodium or ruthenium as well as alloys thereof and nanostructures of noble metals and/or metals, metal oxides and/or additional oxides or carbides.

The application of the electrodes takes place, for instance, by vapor deposit, sputtering or other thin film technologies known to one skilled in the art. The at least one electrode is preferably applied by vapor depositing or sputtering. Furthermore, by multiple application of a thin gas-sensitive layer, it is possible to create a thicker electrode surface, in certain regions, which, having a lower area resistance, makes possible a low-resistance electrical binding of the gas-sensitive layer. This method also permits the forming of rounded edges between the gas-sensitive layer and the electrodes.

The application of at least one gas-sensitive layer also preferably takes place by vapor depositing or sputtering on. Alternatively, the gas-sensitive layer may also be built up as materials which are located in a liquid, gaseous or plasma-like medium, and which, after drying or depositing, form a solid, compact or percolating sensitive layer.

In order to avoid edge breaks from occurring in the contacting region of the electrode with the gas-sensitive layer, it is preferred that the at least one electrode is made of the same material as the at least one gas-sensitive layer. Alternatively, it is also possible to make the at least one electrode of a material which has equal or similar properties to the material of the gas-sensitive layer. It is preferred particularly if the material of the electrode and the material of the gas-sensitive layer have an essentially equal thermal coefficient of expansion. This has the result that the thermal expansion of the gas-sensitive layer and the electrode are essentially the same, so that no edge break at the border surface between the gas-sensitive layer and the electrode takes place.

In order to achieve as good as possible a contact between the electrode and the gas-sensitive layer, it is further preferred if the electrode has a structure having indentations and projections. Because of the indentations and projections, an enlargement of the surface is achieved, whereby a greater contact area comes about between the electrode and the gas-sensitive layer. This has the advantage that even in the case of an edge break in a region of the electrode, other regions continue to contact the gas-sensitive layer, and thus there is no functional loss of the electronic component.

In one example embodiment of the present invention, at least two electrodes contact the gas-sensitive layer, each electrode covering at least a part of the gas-sensitive region.

In the case of two electrodes contacting the gas-sensitive layer, it is possible to measure the electrical contacting of the sensitive layer, as well as the properties of the sensitive layer, such as the constancy of the layer resistance. The measurement can, for instance, take place via a four-point measurement. Because of the possibility of measuring the properties of the gas-sensitive layer, it is possible to detect, early on, possible changes, or even a detachment of the gas-sensitive layer. This makes it possible to exchange the electronic component in good time, before a failure of functioning.

In one example embodiment of the present invention, two electrodes contact the gas-sensitive layer, and the structure of the electrodes is an interdigital structure. In an interdigital structure, each electrode has projections in the form of fingers, the projections reaching into each other like two combs. However, a direct contact of the electrodes is avoided in this context. The region between the electrodes is completely or partially filled out by the material of the gas-sensitive layer. The gas-sensitive layer may alternatively cover the entire sensor region, including the electrodes.

In general, the electronic component according to the present invention includes at least one additional electrode which does not contact the gas-sensitive region. If the electronic component is a field effect transistor, at least two additional electrodes are included that do not contact the gas-sensitive region. The two electrodes in this case are used as a source electrode and a drain electrode.

If the electronic component includes at least one further electrode which does not contact the gas-sensitive region, it is possible to carry out a functional test during operation, via the electrodes. For this purpose, all the electrodes that contact the gas-sensitive layer are expediently put at a specified potential. Electrodes that do not contact the gas-sensitive layer have their potential changed.

The electrodes that do not contact the gas-sensitive region are, for instance, those which lie below or next to the gas-sensitive layer, parallel to the channel or orthogonal to the channel.

Because of the electrode surfaces that do not contact the gas-sensitive layer, changes may be measured at the channel of the signal transmitter. In this way, in particular, changes may be detected at the insulation between the gate region and the channel.

In one example embodiment, the gas-sensitive region of the electronic component is a gate region of a gas-sensitive field effect transistor. Different gases may be detected, depending on the material of the gas-sensitive layer that has been applied on the gas-sensitive region. For instance, in order to detect a plurality of different gases using one gas-sensitive field effect transistor, it is possible, for example, to apply several gas-sensitive layers on the gas-sensitive region. In this case, it is possible, for example, that, using each gas-sensitive layer, a different gas or different components of a gas are able to be detected.

If the gas-sensitive region is a gate region of a gas-sensitive field effect transistor, then preferably the at least one electrode, which contacts the layer of the gas-sensitive material and which covers a part of the gas-sensitive region, is a gate electrode of the field effect transistor.

When the same or a similar material is used for the electrode and the gas-sensitive layer, it is possible, for example, to modify the material of the electrode in such a way that it has a lower specific resistance than the material of the gas-sensitive layer. This has the advantage that possible gas-dependent resistance changes take place predominantly in specified regions outside the electrodes, so that the electrical connection of the sensor region changes only unimportantly.

Furthermore, it is also possible, for example, that the material of which the electrode is made is applied in a greater layer thickness than the material for the gas-sensitive layer. This can be done, for instance, by applying several layers of the material for the electrode. Because of the greater layer thickness of the electrode or the modification of the material for the electrode, for instance, as to the lower specific resistance, it is possible to avoid an edge break at the boundary surface between the gas-sensitive layer and the electrode, for instance under thermal stress.

When a plurality of layers is applied, one may also achieve an edge shape that is optimized to counter edge breaks, such as by rounding it.

Besides the use as a gas-sensitive field effect transistor, the electrode systems described here may also be used in additional chemical gas sensors, for instance, in the form of a CV structure or a Schottky diode.

BRIEF DESCRIPTION OF SEVERAL VIEWS OF THE DRAWING

FIGS. 3.1 to 3.5 show alternative example embodiments for connection of the gate coating of a field effect transistor.

DETAILED DESCRIPTION OF THE INVENTION

Figure 1:
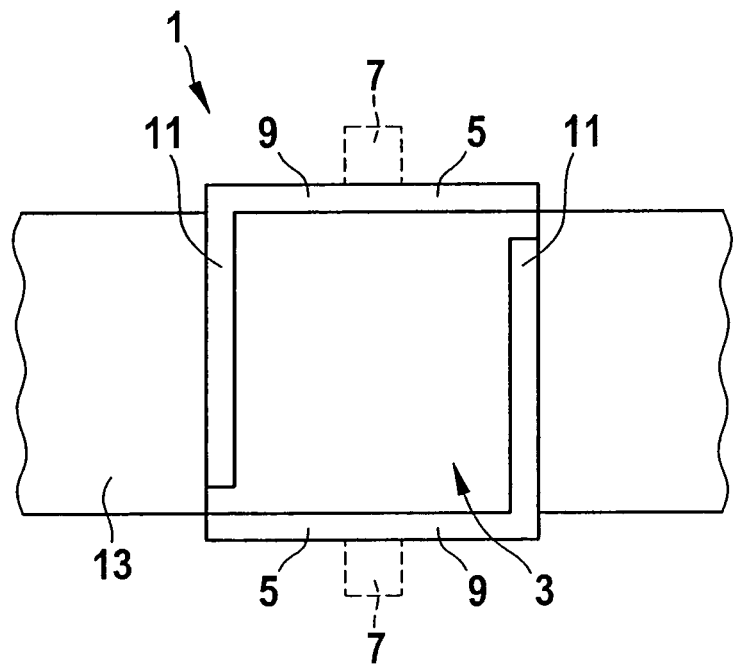
FIG. 1 shows a top view of a first example embodiment of an electronic component developed according to the present invention.

FIG. 1 shows a top view of a first example embodiment of an electronic component developed according to the present invention.

An electronic component 1, which is used for example, as a signal transmitter for the detection of gases, includes a gas-sensitive region 3.

If electronic component 1 is a gas-sensitive field effect transistor, gas-sensitive region 3 is generally the gate region of the field effect transistor. Gas-sensitive region 3 may, for instance, be lined with different gas-sensitive layers. Gas reactions that are as specific as possible are able to be achieved by the different gas-sensitive layers. The gas-sensitive layers generally contain metallic components. These may be catalytically active, at least partially. Alternatively, it is obviously also possible that the entire gas-sensitive layer is made of one catalytically active material.

The metallic components of the gas-sensitive layer are generally at least partially present in nanocrystalline form. Because of the nanocrystalline form, a rapid gas reaction is able to be implemented at, or rather in the gas-sensitive layer, since it is preferably very thin and generally at least partially porous. The layer thicknesses of the gas-sensitive layer may generally be in a range of 10 nm to 10 µm, in this instance.

As the material for the gas-sensitive layers, depending on the gas to be detected or the component of the gas to be detected, a suitable example would be noble metals such as palladium, platinum, gold, rhenium, rhodium or ruthenium, as well as alloys of these and nanostructures of noble metals and/or metals, metal oxides and/or additional oxides or carbides. The material that is suitable in each case for the species to be detected is known to one skilled in the art.

In order to be able to set a specified potential and therewith a working point for the signal transmitter, it is necessary to contact the gas-sensitive layers electrically. The electrical contacting of the gas-sensitive layers is performed, in this instance, by at least one electrode 5. If electronic component 1 is a field effect transistor, electrodes 5 are gate electrodes. The electrical contacting of electrodes 5 in each case takes place via an electrical connection 7. Electrical connection 7 of electrode 5 may be made in any manner known to one skilled in the art, in this context.

Electrode 5 is developed in such a way, according to the present invention, that a part of electrode 5 covers gas-sensitive region 3. In the specific embodiment shown in FIG. 1, electrodes 5 are developed L-shaped for this, a first leg 9 of the electrode being situated outside gas-sensitive region 3, and a second leg 11 being at the edge of gas-sensitive region 3 and lying on top of gas-sensitive region 3. Consequently, a covering of gas-sensitive region 3 by electrode 5 takes place at second leg 11.

The area of gas-sensitive region 3 that is not covered by electrode 5 is coated by the at least one gas-sensitive layer. The gas-sensitive layer borders on electrode 5, in this context. A boundary surface forms between electrode 5 and the gas-sensitive layer. This boundary surface acts as an electrical contact between electrode 5 and the gas-sensitive layer, at the same time.

In order to avoid having an edge break take place at the boundary surface between electrode 5 and the gas-sensitive layer, when thermal stresses occur, it is advantageous to develop electrode 5 and the gas-sensitive layer of the same material. Alternatively, it is also possible, for instance, to develop electrodes 5 and the gas-sensitive layer of two different materials, these having essentially the same thermal coefficient of expansion.

If electrodes 5 and the gas-sensitive layer contain the same material, one may then develop electrodes 5 to a greater layer thickness than the gas-sensitive layer, for example. The greater layer thickness may be achieved, for example, by making a multiple application of the material onto the electrode areas. If the electrodes and the gas-sensitive layer are made of the same material, the electrodes and the gas-sensitive layer may be produced in the same operation, for example. Furthermore, it is also possible, for instance, slightly to modify the material of electrodes 5, in order to achieve a lower resistance at the electrodes, for example. The modification of the material for electrodes 5 takes place, for instance, by adding electrically well conductive material, in this context. This may then be present in the form of an alloy with the material of which the gas-sensitive layer is formed, for instance.

Electronic component 1, which is developed as a field effect transistor, also includes a channel region 13. Channel region 13 generally includes the source connection and the drain connection of the field effect transistor. The source connection and the drain connection generally have no direct contact to the gas-sensitive layer that is contacted by electrodes 5.

Generally speaking, channel region 13 is applied with source connection and drain connection, and electrodes 5 and gas-sensitive region 3 are applied with the corresponding gas-sensitive layers onto a semiconductor material as substrate. As the semiconductor material for the substrate, Si, SiC or (Al)GaN or further semiconductors are used, having a band gap greater than 2 eV.

Because electrodes 5 partially cover gas-sensitive region 3, a functional test is possible, for instance, even during production of the signal transmitter. In particular, a functional test may be carried out even before the gas-sensitive layer is applied onto gas-sensitive region 3. A functional test may be carried out using electronic component 1 even during operation. For this purpose, electrodes 5, which contact the gas-sensitive layer, are put at a specified potential. The source electrode and the drain electrode that are situated in channel region 13, which lie, for example, parallel to channel 13 or orthogonal to the channel, have their potential changed. Because of the electrode surfaces not having connection to the gas-sensitive layer, changes may be measured at channel 13 of the signal transmitter. In particular, changes may be detected at the insulation between the gate region and channel region 13.

In the case of at least two electrodes 5, as shown in FIG. 1, it is furthermore possible to measure the electrical contacting of the gas-sensitive layer as well as its properties, for instance, the constancy of the layer resistance. The measurement then takes place, for instance, via a four-point measurement. In this way, possible changes or a detachment of the layer may be detected early on. A timely exchange of electronic component 1 is made possible thereby.

Figure 2:
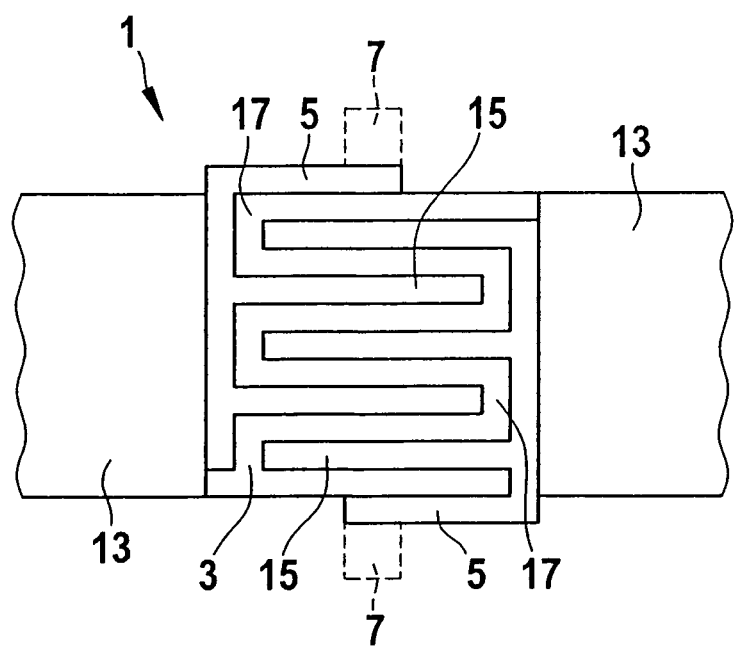
FIG. 2 shows a top view of a second example embodiment of an electronic component developed according to the present invention.

FIG. 2 shows an electronic component 1 in a second example embodiment.

Electronic component 1 shown in FIG. 2 differs from electronic component 1 shown in FIG. 1 by the shape of electrodes 5. By contrast to the L-shaped electrodes 5, as shown in FIG. 1, electrodes 5 according to FIG. 2 each show finger-like projections 15. Between finger-like projections 15, indentations 17 are developed in each case. Two electrodes 5 lie on gas-sensitive region 3, projections 15 of the one electrode in each case meshing with indentations 17 of the other electrode 5. This produces an interdigital structure of electrodes 5. Because of the interdigital structure, a good contact of electrodes 5 with gas-sensitive region 3 and the gas-sensitive layer may be achieved, and small resistances may be achieved in the transition. In addition, because of their structure, the electrodes as shown in FIG. 2 have a very much greater boundary surface with respect to the gas-sensitive layer than is the case for the electrodes according to FIG. 1, for example. Because of this, an edge break, which occurs at one part of the electrode, may be compensated for by the contact in other regions.

Besides the structures of electrodes 5 shown in FIGS. 1 and 2, however, electrodes 5 may also assume any other desired shape. Because of the optional shaping of electrodes 5, it is possible to shape gas-sensitive region 3, which is covered by the gas-sensitive layer, in an optional, desired form. In this way, an exactly defined region may be created, in which the gas-sensitive layer is applied. While shaping electrodes 5, in each case one should only take care that they cover a part of gas-sensitive region 3.

In FIGS. 3.1 to 3.5, top views of alternative example embodiments of a connection of the gate coating according to the present invention are shown.

In FIG. 3.1, electrode 5 is developed annularly for the electrical contacting of gas-sensitive region 3. In this instance, the electrode lies at least partially on the gas-sensitive layer. Electrode 5, in this context, may either lie completely on the gas-sensitive layer, the outer dimensions of the gas-sensitive layer and electrode 5 being equal, or electrode 5 overlaps gas-sensitive region 3.

In the example embodiment shown in FIG. 3.2, electrodes 5 are developed so that in each case they cover approximately one-third of gas-sensitive region 3. Electrodes 5 are developed to be rectangular, in this context.

One example embodiment having L-shaped electrodes 5 is shown in FIG. 3.3. The example embodiment shown in FIG. 3.3 corresponds essentially to the example embodiment shown in FIG. 1. However, based on the rectangular shaping of gas-sensitive region 3, the area of gas-sensitive region 3 that is not covered by electrodes 5 is smaller than in the example embodiment shown in FIG. 1.

Two additional example embodiments are shown in FIGS. 3.4 and 3.5. In this case, the electrodes are in each case developed in the form of an interdigital structure on a rectangular gas-sensitive region 3, in which electrodes 5 mesh with each other using finger-like projections. The projections, in this context, are developed in one case, as shown in FIG. 3.4, in the direction of electrical connections 7, and, in the other case, as shown in FIG. 3.5, transversely to electrical connections 7. This means that, in the example embodiment shown in FIG. 3.4, the current flow of the field effect transistor in the gate region runs transversely to the fingers of electrodes 5, and in FIG. 3.5 it runs in the direction of the fingers of electrodes 5.

What is claimed is:

1. An electronic component, comprising:
   at least one gas-sensitive region provided on a substrate, wherein the gas-sensitive region is coated by at least one electrically conductive, gas-sensitive layer; and
   at least one electrode positioned above the at least one gas-sensitive region, wherein the at least one electrode contacts the upper surface of the gas-sensitive layer, and wherein at least a part of the at least one electrode covers a part of the upper surface of the gas-sensitive region;
   wherein the at least one electrode is made of the same material as the at least one gas-sensitive layer.

2. The electronic component as recited in claim 1, wherein the at least one electrode includes one of palladium, platinum, gold, rhenium, rhodium, ruthenium, titanium, titanium nitride or tantalum nitride.

3. An electronic component, comprising:
   at least one gas-sensitive region provided on a substrate, wherein the gas-sensitive region is coated by at least one electrically conductive, gas-sensitive layer; and
   at least one electrode positioned above the at least one gas-sensitive region, wherein the at least one electrode contacts the upper surface of the gas-sensitive layer, and wherein at least a part of the at least one electrode covers a part of the upper surface of the gas-sensitive region;
   wherein the at least one electrode includes one of palladium, platinum, gold, rhenium, rhodium, ruthenium, titanium, titanium nitride or tantalum nitride;
   wherein the at least one gas-sensitive layer includes at least one of palladium, platinum, gold, rhenium, rhodium, ruthenium, and nanostructures of noble metals.

4. The electronic component as recited in claim 3, wherein the at least one electrode is made of the same material as the at least one gas-sensitive layer.

5. The electronic component as recited in claim 3, wherein the at least one electrode has a structure including indentations and projections, in order to provide a large contact surface with respect to the gas-sensitive layer.

6. The electronic component as recited in claim 3, wherein at least two electrodes are provided and contact the gas-sensitive layer, and wherein each electrode covers at least a part of the gas-sensitive region.

7. The electronic component as recited in claim 6, wherein the two electrodes have an overall interdigital structure and contact the gas-sensitive layer.

8. The electronic component as recited in claim 3, wherein the gas-sensitive region is a gate region of a gas-sensitive field effect transistor.

9. The electronic component as recited in claim 3, wherein the material of the at least one electrode is modified to have a lower specific resistance relative to the material of the gas-sensitive layer.

10. An electronic component, comprising:
    at least one electrode; and
    at least one gas-sensitive region provided on a substrate;
    wherein:
       the gas-sensitive region is coated by at least one electrically conductive, gas-sensitive layer;
       the at least one gas-sensitive layer includes at least one of palladium, platinum, gold, rhenium, rhodium, ruthenium, and nanostructures of noble metals;
       the at least one electrode contacts the gas-sensitive layer;
       the at least one electrode includes one of palladium, platinum, gold, rhenium, rhodium, ruthenium, titanium, titanium nitride or tantalum nitride;
       at least a part of the at least one electrode covers a part of the gas-sensitive region;
       the gas-sensitive region is a gate region of a gas-sensitive field effect transistor; and
       the at least one electrode is a gate electrode.

* * * * *